United States Patent
McLendon et al.

(10) Patent No.: US 12,252,463 B2
(45) Date of Patent: Mar. 18, 2025

(54) COMPOSITIONS AND METHODS OF MAKING RIBITOL

(71) Applicant: THE CHARLOTTE MECKLENBURG HOSPITAL AUTHORITY, Charlotte, NC (US)

(72) Inventors: George L. McLendon, Davidson, NC (US); Bas Wilhelmus Theodorus Gruijters, Gemert (NL); Qi Long Lu, Charlotte, NC (US)

(73) Assignee: THE CHARLOTTE MECKLENBURG HOSPITAL AUTHORITY, Charlotte, NC (US)

( * ) Notice: Subject to any disclaimer, the term of this patent is extended or adjusted under 35 U.S.C. 154(b) by 765 days.

(21) Appl. No.: 17/613,903

(22) PCT Filed: May 27, 2020

(86) PCT No.: PCT/US2020/034732
§ 371 (c)(1),
(2) Date: Nov. 23, 2021

(87) PCT Pub. No.: WO2020/243190
PCT Pub. Date: Dec. 3, 2020

(65) Prior Publication Data
US 2022/0227692 A1 Jul. 21, 2022

Related U.S. Application Data

(60) Provisional application No. 62/853,316, filed on May 28, 2019.

(51) Int. Cl.
C07C 31/18 (2006.01)
C07C 29/14 (2006.01)

(52) U.S. Cl.
CPC .............. *C07C 31/18* (2013.01); *C07C 29/14* (2013.01)

(58) Field of Classification Search
CPC .................................................... C07C 31/18
See application file for complete search history.

(56) References Cited

U.S. PATENT DOCUMENTS

| | | |
|---|---|---|
| 10,245,235 B2 | 4/2019 | Lu |
| 10,434,072 B2 | 10/2019 | Lu |
| 10,434,113 B2 | 10/2019 | Lu et al. |
| 10,456,367 B2 | 10/2019 | Lu |
| 10,993,954 B2 | 5/2021 | Lu et al. |
| 11,931,371 B2 | 3/2024 | Lu et al. |
| 2007/0181437 A1 | 8/2007 | Stapley et al. |
| 2018/0169036 A1 | 6/2018 | Lu |
| 2019/0008881 A1 | 1/2019 | Lu et al. |
| 2020/0061092 A1 | 2/2020 | Lu et al. |
| 2023/0364118 A1 | 11/2023 | Lu |

FOREIGN PATENT DOCUMENTS

| | | |
|---|---|---|
| CN | 101050225 A | 10/2007 |
| CN | 109640947 A | 4/2019 |
| JP | H114699 A | 1/1999 |
| JP | H11137285 A | 5/1999 |
| JP | 2009526131 A | 7/2009 |
| WO | WO-2007092079 A2 | 8/2007 |
| WO | WO-2018025089 A2 | 2/2018 |

OTHER PUBLICATIONS

U.S. Appl. No. 18/438,820, filed Feb. 12, 2024, by Qi Long Lu et al.
U.S. Appl. No. 15/842,580, filed Dec. 14, 2017, U.S. Pat. No. 10,245,235, Apr. 2, 2019.
U.S. Appl. No. 16/112,447, filed Aug. 24, 2018, U.S. Pat. No. 10,434,113, Oct. 8, 2019.
U.S. Appl. No. 16/151,113, filed Dec. 14, 2017, U.S. Pat. No. 10,434,072, Oct. 8, 2019.
U.S. Appl. No. 16/151,126, filed Dec. 14, 2017, U.S. Pat. No. 10,456,367, Oct. 29, 2019.
U.S. Appl. No. 16/554,338, filed Aug. 28, 2019, U.S. Pat. No. 10,993,954, May 4, 2021.
U.S. Appl. No. 17/222,662, filed Apr. 5, 2021, U.S. Pat. No. 11,931,371, Mar. 19, 2024.
U.S. Appl. No. 18/438,820, filed Feb. 12, 2024.
U.S. Appl. No. 16/549,986, filed Aug. 23, 2019.
U.S. Appl. No. 18/044,747, filed Sep. 9, 2021.
Argyropoulos, N.G., et al., "Synthesis of Enantiomerically Pure Hydroxylated Pyrroline N-oxides from D-ribose", Tetrahedron Asymmetry, Pergamon Press, Mar. 6, 2006, vol. 17, No. 5, pp. 829-836.
Bien, S., et al., "The Structure of Bornesitol", Journal of the Chemical society, Jan. 1, 1958, pp. 3189-3194.
Cataldi, M.P., et al., "Ribitol Restores Functionally Glycosylated Alpha-dystroglycan and Improves Muscle Function in Dystrophic FKRP-Mutant Mice", Nature Communications, Aug. 27, 2018, vol. 9, No. 1, 12 pages.
Crum, J.D., et al., "The Synthesis of D-Erythro-Pentulose", Dissertation, The Ohio State University, Jan. 1, 1958, pp. 1-116, XP055876945, <URL:https://etd.ohiolink.edu/apexprod/rws_etd/send_file/send?accession=osu1486470182524888&disposition=inline>.
David, S., et al., "[Distribution of the radioactivity in biosynthesized D-ribose]" (article in French), Biochimica et biophysica acta, vol. 16, Jan. 1, 1955, pp. 598-599, XP025667447, ISSN: 0006-3002, DOI: 10.1016/0006-3002(55)90289-4, p. 598, with machine translation, 4 pages.
Extended European Search Report for European Application No. EP20812854.6 dated Jun. 2, 2023, 13 pages.

(Continued)

*Primary Examiner* — Golam M Shameem
(74) *Attorney, Agent, or Firm* — COOLEY LLP

(57) ABSTRACT

The present disclosure describes compositions comprising substantially pure ribitol, pharmaceutical compositions of ribitol, and methods of making ribitol. The methods may include combining a reducing agent (e.g., borohydride) and ribose (e.g. D-ribose), optionally with stirring, to form a first reaction mixture; and contacting the first reaction mixture and an acidic quenching agent, optionally with stirring, to form a second reaction mixture, thereby forming ribitol.

11 Claims, 1 Drawing Sheet

(56) References Cited

OTHER PUBLICATIONS

Garrette, C., et al., "(1-13C)alditols: elimination of magnetic equivalence in $^1$H- and $^{13}$C-n.m.r. spectra of symmetric compounds through ($^{13}$C)-substitution," Carbohydrate Research, Dec. 15, 1990, vol. 208, pp. 23-35.

Sevestre, A., et al., "Synthesis of Stereochemical Probes for New Fluorogenic Assays for Yeast Transketolase Variants", Tetrahedron, vol. 62, No. 17, Apr. 24, 2006, pp. 3969-3976.

Abdel-Akher et al., "The Reduction of Sugars with Sodium Borohydride," Journal of the American Chemical Society, vol. 73, No. 10, Oct. 10, 1951, Aug. 5, 2020, retrieved from the Internet https://pubs.acs.org/doi/abs/10.1021/ja01154a061, abstract, p. 4691.

Crum, "The Synthesis of D-Erythro-Pentulose," Ph.D. Dissertation, 1958, retrieved from the Internet URL:etd.ohiolink.edu/!etd.send_file?accession=osu1486470182524888&disposition=inline, pp. 49-51, 81-82.

International Search Report and Written Opinion for International Application No. PCT/US2020/034732, dated Sep. 8, 2020, 9 pages.

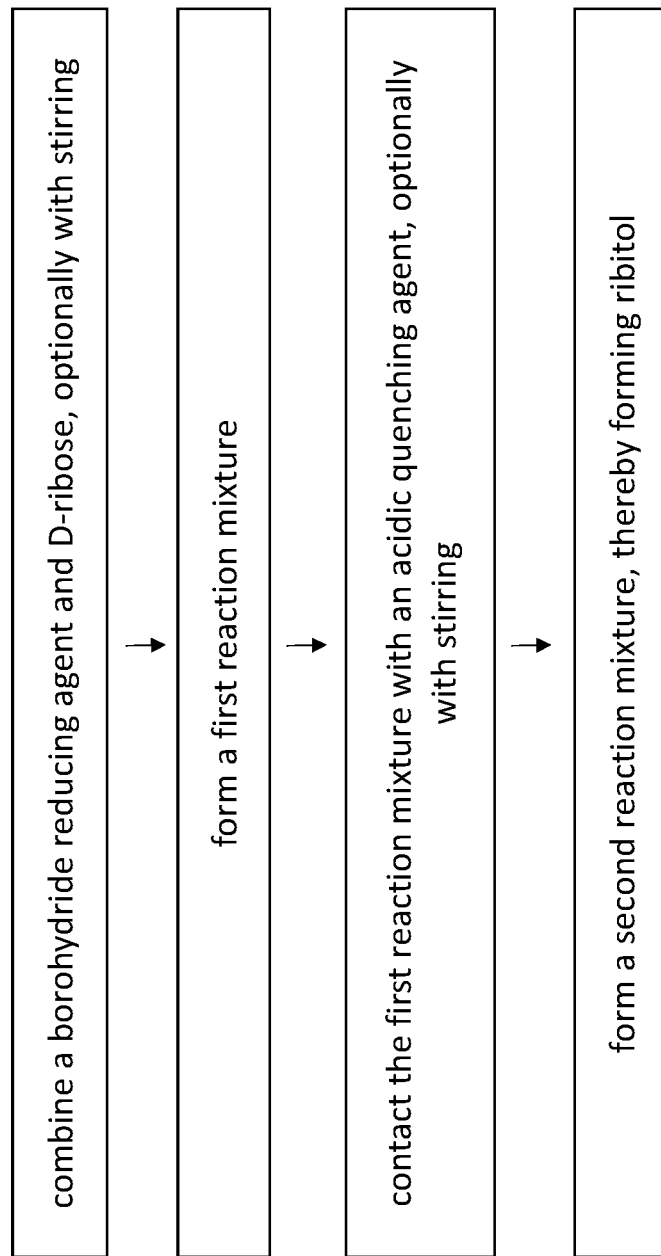

COMPOSITIONS AND METHODS OF MAKING RIBITOL

CROSS-REFERENCE TO RELATED APPLICATIONS

This application is a 35 U.S.C. § 371 national phase application of International Patent Application No. PCT/US2020/034732, filed May 27, 2020, which claims priority under 35 U.S.C. § 119 (e) to U.S. Provisional Patent Application No. 62/853,316, filed May 28, 2019. The disclosure of each of these applications is incorporated herein by reference in its entirety.

FIELD OF THE INVENTION

The present disclosure generally relates to compositions and methods for making ribitol and to compositions comprising ribitol including ribitol having a high purity and/or a low concentration of impurities.

BACKGROUND OF THE INVENTION

The reduction of D-ribose to ribitol is most often described in literature by the process of catalytic hydrogenation. Raney nickel is the catalyst of choice although platinum on carbon and ruthenium on carbon are also found to be viable alternatives. Water, alcohols and mixtures thereof are used as solvent systems. Drawbacks of this approach are the expensive catalysts and the necessity to purge residual metals from the catalyst to low levels.

Hydrogenation can also be effected by transfer hydrogenation. Although no specific literature appears available for the conversion of D-ribose to ribitol, a variety of comparable sugars have been reported to successfully deliver their reduced derivatives after being subjected to transfer hydrogenation conditions. Ruthenium ligand complexes are almost exclusively with secondary alcohols (2-propanol, 2-butanol, etc.) acting as hydrogen donors. Likely drawbacks of this approach are the same as described for the catalytic hydrogenation process.

It is also known to use sodium borohydride as a reducing agent for generating ribitol using water as solvent. Sodium borohydride is a relatively cheap and effective reagent, which is an advantage over the metal-catalyzed processes. However, the development of a robust and scalable isolation procedure starting from an aqueous mixture is very challenging considering the hydrophilic nature of ribitol.

SUMMARY OF THE INVENTION

A first aspect of the present disclosure is directed to a method of making ribitol. The method may comprise combining a reductive borohydride and D-ribose, optionally with stirring, to form a first reaction mixture; and contacting the first reaction mixture and an acidic quenching agent, optionally with stirring, to form a second reaction mixture, thereby forming ribitol.

A further aspect of the present disclosure is directed to ribitol prepared according to the methods described herein.

Another aspect of the present disclosure is directed to ribitol having a purity of at least 90%. In some embodiments, the ribitol comprises less than about 5,000 ppm of lithium, sodium, and/or a salt thereof; less than about 20,000 ppm of an acidic quenching agent and/or an anionic derivative thereof; less than about 5,000 ppm of an organic solvent; and/or less than about 3,000 ppm of boron.

Another aspect of the present disclosure is directed to a composition comprises substantially pure ribitol. In some embodiments, the composition is substantially free of nickel, platinum, palladium, ruthenium, sodium, boric acid, trifluoroacetic acid, D-Arabitol and/or any combination thereof. The composition may be a pharmaceutical composition or a unit dosage form.

It is noted that aspects of the disclosure described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present disclosure are explained in detail in the specification set forth below. Further features, advantages and details of the present disclosure will be appreciated by those of ordinary skill in the art from a reading of the figures and the detailed description of the preferred embodiments that follow, such description being merely illustrative of the present disclosure.

BRIEF DESCRIPTION OF THE DRAWINGS

FIG. 1 is a flow chart schematic of a first aspect of the present disclosure directed to a new method of ribitol synthesis.

DETAILED DESCRIPTION OF THE INVENTION

The drawbacks of known approaches to ribitol synthesis are incomplete conversion, difficulty in scaling, and the presence of toxic side products and residual catalyst metals that are not safe for patient administration.

The inventors have developed a viable route to ribitol suitable for pharmaceutical application in both yield and purity. Through extensive experimentation, the inventors have recognized that, although conversion of D-ribose to ribitol using sodium borohydride in water can be achieved in high yield, the solubility of ribitol in water prevents product crystallization even after addition of large quantities of anti-solvent. Moreover, quenching of the reaction with strong acids or inorganic acids, such as hydrogen chloride, may make the product not suitable for use as a pharmaceutical.

Disclosed herein are novel synthetic routes to ribitol that produce ribitol with yield and purity suitable for manufacture of pharmaceutical products. The disclosed methods may include one or more of (i) use of an organic solvent, e.g., an alcohol; (ii) use of an organic acid; (iii) use of a weak acid; and/or (iv) recrystallization of the ribitol from the organic solvent. In some cases, specified impurities are below predetermined thresholds.

The disclosed methods have many advantages including spontaneous crystallization, ease of scalability, and a high yield of a highly pure ribitol. The disclosed compositions may, advantageously, be used in preparation of pharmaceutical compositions and in other applications where high yield and/or purity is desirable. Substantially pure ribitol is desirable for the preparation of a pharmaceutical grade composition. The pure ribitol used may advantageously be: (i) free from impurities, which may be toxic; (ii) free from residual metals, which may also be toxic; (iii) synthesized using a process that can be scaled without laborious and time-consuming procedures.

A method is needed to generate a high yielding and highly pure ribitol acceptable for dosing in gram quantities for pharmacological treatment. Such a method should be able to obtain high conversion levels from ribose to ribitol without the formation of impurities.

Thus, there is a need for a ribitol composition that is highly pure and a process to produce such ribitol that does not require the use of metal catalysts or aqueous solvents. The present disclosure is directed to satisfying this need.

The present disclosure is now described more fully hereinafter with reference to the accompanying drawings, in which embodiments of the disclosure are shown. This disclosure may, however, be embodied in many different forms and should not be construed as limited to the embodiments set forth herein; rather these embodiments are provided so that this disclosure will be thorough and complete and will fully convey the scope of the disclosure to those skilled in the art.

As used in the description of the disclosure and the appended claims, the singular forms a, an, and the are intended to include the plural forms as well, unless the context clearly indicates otherwise.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the disclosure herein is for the purpose of describing particular embodiments only and is not intended to be limiting of the disclosure. All publications, patent applications, patents and other references mentioned herein are incorporated by reference in their entirety. In case of a conflict in terminology, the present specification is controlling.

Also as used herein, and/or refers to and encompasses any and all possible combinations of one or more of the associated listed items, as well as the lack of combinations when interpreted in the alternative (or).

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase consisting essentially of (and grammatical variants) is to be interpreted as encompassing the recited materials or steps and those that do not materially affect the basic and novel characteristic(s) of the claimed invention. See, In re Herz, 537 F.2d 549, 551-52, 190 U.S.P.Q. 461, 463 (CCPA 1976) (emphasis in the original); see also MPEP § 2111.03. Thus, the term consisting essentially of as used herein should not be interpreted as equivalent to comprising.

It will also be understood that, as used herein, the terms example, exemplary, and grammatical variations thereof are intended to refer to non-limiting examples and/or variant embodiments discussed herein, and are not intended to indicate preference for one or more embodiments discussed herein compared to one or more other embodiments.

The term about, as used herein when referring to a measurable value such as an amount or concentration and the like, is meant to encompass variations of ±10%, ±5%, ±1%, ±0.5%, or even ±0.1% of the specified value as well as the specified value. For example, about X where X is the measurable value, is meant to include X as well as variations of ±10%, ±5%, ±1%, ±0.5%, or even ±0.1% of X. A range provided herein for a measureable value may include any other range and/or individual value therein.

As used herein, the terms increase, increases, increased, increasing, enhance, and similar terms indicate an elevation in the specified parameter of at least about 2%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more unless otherwise specifically noted within the text.

As used herein, the terms reduce, reduces, reduced, reduction, inhibit, and similar terms refer to a decrease in the specified parameter of at least about 2%, 5%, 10%, 15%, 20%, 25%, 30%, 35%, 40%, 45%, 50%, 55%, 60%, 65%, 70%, 75%, 80%, 85%, 90%, 95%, 97%, or 100% unless otherwise specifically noted within the text.

Embodiments of the present disclosure are directed to a method of making ribitol. The method may comprise combining a reductive borohydride and D-ribose to form a first reaction mixture; and contacting the first reaction mixture and an acidic quenching agent to form a second reaction mixture, thereby forming ribitol. D-ribose may be reduced to ribitol in the first reaction mixture. The reductive borohydride and D-ribose may be combined with stirring and/or the first reaction mixture may be contacted with an acidic quenching agent with stirring.

"Contact", "contacting", "contacted," and grammatical variations thereof, as used herein refer to bringing two or more materials (e.g., a composition, compound, solvent, etc.) together to form a mixture. Contacting the two or more materials may be carried out by placing, adding, combining, pouring, spraying, mixing, flowing, injecting, and/or the like one or both of the materials to bring them together to form a mixture. For example, in some embodiments, contacting the first reaction mixture and an acidic quenching agent may comprise adding an acidic quenching agent to the first reaction mixture.

In some embodiments, the first reaction mixture may comprise a solvent (e.g., an organic solvent). The solvent may be present in a relative volume (e.g., L/kg or mL/g) of about 1 or 2 to about 3, 4, 5, 6, 7, 8, 9 or 10 compared to D-ribose. For example, in some embodiments, the solvent is present in a relative volume of about 1 or 2 to about 3 compared to D-ribose. In some embodiments, the solvent is present in a relative volume (e.g., L/kg or mL/g) of about 1 or 2 to about 10 compared to D-ribose. In some embodiments, the solvent is present in a relative volume (e.g., L/kg or mL/g) of about 1, 2, 3, 4, 5, 6, 7, 8, 9, or 10 compared to D-ribose. The second reaction mixture may comprise a solvent (e.g., an organic solvent).

In some embodiments, the first and/or second reaction mixtures are non-aqueous or free of water. In some embodiments, the first reaction mixture and the second reaction mixture are non-aqueous or free of water. In some embodiments, the method of making ribitol according to embodiments of the present disclosure is carried out with non-aqueous compositions. In some embodiments, the first and/or second reaction mixtures comprise an organic solvent.

Exemplary organic solvents include, but are not limited to, ethanol, methanol, propanol (e.g., 1-propanol, 2-propanol), ethylenediamine, water:pyridine:methanol (1:1:1) and/or any combination thereof. In some embodiments, the organic solvent is methanol. In some embodiments, the organic solvent is ethanol. In some embodiments, the organic solvent is 1-propanol.

Illustrative reductive borohydrides include, but are not limited to, lithium borohydride ($LiBH_4$), sodium borohydride ($NaBH_4$), zinc borohydride ($Zn(BH_4)_2$), calcium borohydride ($Ca(BH_4)_2$), sodium triacetoxyborohydride ($NaBH(OAc)_3$), sodium cyanoborohydride ($NaBH_3CN$), potassium borohydride ($KBH_4$), and/or any combination thereof. In some embodiments, the reductive borohydride is lithium borohydride ($LiBH_4$). In some embodiments, the reductive borohydrides is provided in liquid form, i.e. in solution. Suitable solvents for the reducing agent include tetrahydrofuran (THF), an alcohol (e.g., methanol, ethanol, or isopropyl alcohol), dimethyl ether of diethylene glycol, dimethyl ether of triethylene glycol, anhydrous ether, diglyme methanol, mixed solvents containing methanol (e.g., nitro, chloro, or amide groups in ether containing a small amount of methanol), diethyl ether, or any combination thereof. In some embodiments, the lithium borohydride is in solid form. In some embodiments, both liquid and solid lithium borohydride may be used in one or more reaction mixtures. In some embodiments, the reductive borohydride is sodium borohydride ($NaBH_4$). In some embodiments, the reducing agent is an aluminum hydride. In some embodiments, the reductive aluminum hydride is lithium-aluminum hydride.

In some embodiments, prior to combining a reductive borohydride and D-ribose, the D-ribose may be present in a composition comprising D-ribose and an organic solvent (e.g., an alcoholic solvent). The composition may be a suspension comprising D-ribose suspended in the organic solvent.

In some embodiments, contacting the first reaction mixture and the acidic quenching agent may comprise adding the acidic quenching agent in a sub-stoichiometric amount relative to D-ribose, for example, adding the acidic quenching agent in 0.5 molar equivalents. In some embodiments, the acidic quenching agent may be in an amount of about 0.3 to about 0.6 molar equivalents relative to D-ribose. For example, in some embodiments, the acidic quenching agent may be in an amount of about 0.3 or 0.4 to about 0.5 or 0.6 molar equivalents relative to D-ribose. In some embodiments, the acidic quenching agent may be in an amount of about 0.3, 0.4, 0.5, or 0.6 molar equivalents relative to D-ribose. In some embodiments, contacting the first reaction mixture and the acidic quenching agent may comprise contacting a solid or liquid acidic quenching agent with the first reaction mixture.

Illustrative acidic quenching agents include, but are not limited to, citric acid, formic acid, acetic acid, isophthalic acid, trifluoroacetic acid, hydrochloric acid, oxalic acid, propionic acid, pyruvic acid, methanesulfonic acid, trifluoromethanesulfonic acid, a C1-5 carboxylic or dicarboxylic acid and/or any combination thereof. In some embodiments, the acidic quenching agent is an organic carboxylic acid. In some embodiments, the acidic quenching agent is citric acid. In some embodiments, the acidic quenching agent is trifluoroacetic acid. In some embodiments, the acidic quenching agent is an acid with a pKa greater than 0, greater than 0.25, greater than 0.5, greater than 1, or greater than 2. In some embodiments, the acidic quenching agent is an acid with a pKa less than 0, less than 0.25, less than 0.5, less than 1, or less than 2.

In some embodiments, lithium borohydride and D-ribose are combined to form a first reaction mixture; and the first reaction mixture is contacted with citric acid to form ribitol.

In some embodiments, combining the reductive borohydride and D-ribose may comprise adding a total amount of the reductive borohydride in one or more (e.g., 1, 2, 3, 4, 5, or more) portion(s) to D-ribose over a period of time. In some embodiments, the reductive borohydride is added to D-ribose in at least two separate portions. In some embodiments, the reductive borohydride may be added to D-ribose over a period of time of about 5 minutes to about 200 minutes. For example, in some embodiments, the reductive borohydride may be added to D-ribose over about 5, 10, 20, 30, 40, 50, 60, 70, 80, 90, or 100 minutes to about 110, 120, 130, 140, 150, 160, 170, 180, 190, or 200 minutes. In some embodiments, the reductive borohydride is added to D-ribose in a period of time of about 5, 10, 20, 30, 40, 50, 60, 70, 80, 90, 100, 110, 120, 130, 140, 150, 160, 170, 180, 190, or 200 minutes.

In some embodiments, combining the reductive borohydride and D-ribose may be carried out at a temperature of about 5° C. to about 35° C. For example, in some embodiments, combining the reductive borohydride and D-ribose may be carried out at a temperature of about 5° C., 10° C., or 15° C. to about 20° C., 30° C., or 35° C. In some embodiments, combining the reductive borohydride and D-ribose may be carried out at a temperature of about 5° C., 10° C., 15° C., 20° C., 30° C., or 35° C. In some embodiments, combining reductive borohydride and D-ribose may be carried out under cooling conditions.

A method of making ribitol according to embodiments of the present disclosure may comprise stirring the first reaction mixture. In some embodiments, the method may comprise stirring the first reaction mixture for about 1 hour to about 30 hours. For example, in some embodiments, the method may comprise stirring the first reaction mixture for about 1, 2, 3, 4, 5, 6, 7, 8, 9, 10, 11, 12, 13, or 14 hours to about 15, 16, 17, 18, 19, 20, 21, 22, 23, 24, 25, 26, 27, 28, 29 or 30 hours. In some embodiments, the method may comprise stirring the first reaction mixture for about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours.

A method of making ribitol according to embodiments of the present disclosure may comprise stirring the second reaction mixture. In some embodiments, the method may optionally comprise stirring the second reaction mixture for about 1 hour to about 30 hours. For example, in some embodiments, the method may comprise stirring the second reaction mixture for about 1, 2, 3, 4, 5, 6, 7, 8, 9, 10, 11, 12, 13, or 14 hours to about 15, 16, 17, 18, 19, 20, 21, 22, 23, 24, 25, 26, 27, 28, 29, or 30 hours. In some embodiments, the method may comprise stirring the second reaction mixture for about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours. In some embodiments, the method may comprise stirring the second reaction mixture at a temperature of about 5° C. to about 35° C. For example, in some embodiments, the method may comprise stirring the second reaction mixture at a temperature of about 5° C., 10° C., or 15° C. to about 20° C., 30° C., or 35° C. In some embodiments, the method may comprise stirring the second reaction mixture at a temperature of about 5° C., 10° C., 15° C., 20° C., 30° C., or 35° C.

A method of making ribitol according to embodiments of the present disclosure may comprise heating the second reaction mixture. In some embodiments, the method may comprise heating the second reaction mixture to a temperature of about 40° C. to about 65° C. For example, in some embodiments, the method may comprise heating the second reaction mixture to a temperature of about 40° C., 45° C., or 50° C. to about 55° C., 60° C., or 65° C. In some embodiments, the method may comprise heating the second reaction mixture to a temperature of about 40° C., 45° C., 50° C., 55° C., 60° C., or 65° C. In some embodiments, the method may comprise heating the second reaction mixture for about 1 minute to about 30 minutes. For example, in some embodiments, the method may comprise heating the second reaction mixture for about 1, 2, 3, 4, 5, 6, 7, 8, 9, 10, 11, 12, 13, or 14 minutes to about 15, 16, 17, 18, 19, 20, 21, 22, 23, 24, 25, 26, 27, 28, 29 or 30 minutes. In some embodiments, the method may comprise heating the second reaction mixture for about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 minutes. In some embodiments, heating the second reaction mixture may be done while stirring the second reaction mixture.

In some embodiments, a method of making ribitol comprises precipitating ribitol from the second reaction mixture. In some embodiments, ribitol may spontaneously crystallize. In some embodiments, ribitol may spontaneously crystallize after an acid quench.

In some embodiments, the second reaction mixture may comprise about 1 to about 5 relative volumes of an organic solvent (e.g., methanol). For example, in some embodiments, the second reaction mixture may comprise about 1 or 2 to about 3, 4, or 5 relative volumes of an organic solvent. In some embodiments, the second reaction mixture may comprise about 1 2, 3, 4, or 5 relative volumes of an organic solvent. In some embodiments, the second reaction mixture may comprise an acid quench that is carried out in about 1 to about 5 relative volumes of an organic solvent (e.g., methanol). For example, in some embodiments, an acid quench is carried out in about 1 or 2 to about 3, 4, or 5 relative volumes of an organic solvent.

A method of making ribitol according to embodiments of the present disclosure may comprise isolating ribitol from the second reaction mixture to obtain an isolated ribitol. "Isolating" and grammatical variations thereof as used herein refer to at least partially separating or removing one component from one or more component(s) such as, e.g., separating ribitol from a second reaction mixture. Methods of isolating compounds from mixtures are known in the art and include, but are not limited to, filtration, evaporation, and/or the like. In some embodiments, isolating ribitol comprises filtering ribitol from a mixture (e.g., a second reaction mixture) and/or evaporating a solvent from a mixture in which ribitol is present.

In some embodiments, a method of making ribitol comprises washing the isolated ribitol with a wash solvent. Exemplary wash solvents include, but are not limited to, organic solvents such as ethanol, methanol, propanol (e.g., 1-propanol, 2-propanol) and/or any combination thereof. In some embodiments, the wash solvent is 1-propanol. In some embodiments, a method of making ribitol comprises recrystallizing isolated ribitol with an organic solvent such as, but not limited to, those described herein.

According to some embodiments, a method of the present disclosure comprising combining lithium borohydride and D-ribose to form a first reaction mixture; and contacting the first reaction mixture and an acidic quenching agent comprising citric acid to form a second reaction mixture, thereby forming ribitol. The ribitol may be washed with a wash solvent comprising 1-propanol.

In various embodiments, the disclosure provides compositions comprising ribitol and optionally one or more impurities at about 0% to about 0.05%, about 0.1%, about 0.2%, about 0.3%, about 0.4%, or about 0.5%. Total impurities in the ribitol composition may be less than about 0.05%, about 0.1%, about 0.2%, about 0.3%, about 0.4%, or about 0.5%. The impurity D-arabitol may be present at about 0% to about 0.05%, about 0.1%, about 0.2%, about 0.3%, about 0.4%, or about 0.5%. Total D-arabitol in the ribitol composition may be less than about 0.05%, about 0.1%, about 0.2%, about 0.3%, about 0.4%, or about 0.5%.

The impurity D-ribose may be present at about 0% to about 0.05%, about 0.1%, about 0.2%, about 0.3%, about 0.4%, or about 0.5%. Total D-ribose in the ribitol composition may be less than about 0.05%, about 0.1%, about 0.2%, about 0.3%, about 0.4%, or about 0.5%.

In some embodiments, the methods of the disclosure provide ribitol compositions having elemental impurities at or below the following thresholds: $Cd \leq 0.5$ ppm; $Pb \leq 0.5$ ppm; $As \leq 1.5$ ppm; $Hg \leq 3$ ppm; $Co \leq 5$ ppm; $V \leq 10$ ppm; $Ni \leq 20$ ppm; $Boron \leq 1000$ ppm; $Lithium \leq 55$ ppm.

The ribitol compositions of the disclosure may comprises lithium, sodium, or boron, each one at below 10 ppm, 20 ppm, 30 ppm, 40 ppm, 50 ppm, 60 ppm, 70 ppm, 80 ppm, 90 ppm, 100 ppm, 500 ppm, 750 ppm, or 1000 ppm.

Ribitol of the present disclosure (e.g., an isolated ribitol) may comprise less than about 5,000 ppm of lithium, sodium, and/or a salt thereof. For example, in some embodiments, ribitol may comprise less than 5,000, 4,000, 3,000, 2,000, 1,500, 1,000, 500, 400, 300, 200, 100, or 10 ppm of lithium, sodium, and/or a salt thereof. In some embodiments, ribitol comprises less than 500 ppm of lithium, sodium, and/or a salt thereof. In some embodiments, ribitol comprises less than 500 ppm of lithium and/or a salt thereof. In some embodiments, recrystallized ribitol comprises less than 10 ppm of lithium and/or a salt thereof.

Ribitol of the present disclosure (e.g., an isolated ribitol) may comprise less than about 30,000 ppm of an acidic quenching agent and/or an anionic derivative thereof. For example, in some embodiments, ribitol comprises less than about 30,000, 25,000, 20,000, 15,000, 10,000, 5,000, 4,000, 3,000, 2,000, 1,500, 1,000, 500, 100, or 10 ppm of an acidic quenching agent and/or an anionic derivative thereof. In some embodiments, ribitol comprises less than about 20,000 ppm of the acidic quenching agent and/or an anionic derivative thereof. In some embodiments, ribitol comprises less than about 4,000 ppm of an acidic quenching agent and/or an anionic derivative thereof.

Ribitol of the present disclosure (e.g., an isolated ribitol) may comprise less than about 10,000 ppm of an organic solvent and/or wash solvent. For example, in some embodiments, ribitol comprises less than 10,000, 9,000, 8,000, 7,000, 6,000, 5,000, 4,000, 3,000, 2,000, 1,500, 1,000, 500, 100, or 10 ppm of an organic solvent and/or wash solvent. In some embodiments, ribitol comprises less than 5,000 or 3,000 ppm of an organic solvent. In some embodiments, ribitol comprises less than 5,000 ppm of propanol (e.g., 1-propanol, 2-propanol). In some embodiments, ribitol comprises less than 3,000 ppm of methanol.

Ribitol of the present disclosure (e.g., an isolated ribitol) may comprise less than 3,000, 2,000, 1,500, 1,000, 500, or 100 ppm of boron. For example, in some embodiments, ribitol comprises less than about 3,000, 2,000, 1,500, 1,000, 500, 100, or 10 ppm of boron. In some embodiments, ribitol comprises less than about 1,000 ppm of boron.

In some embodiments, a method of the present disclosure provides ribitol (e.g., isolated ribitol) in a yield of at least about 60%. For example, in some embodiments, ribitol may be obtained and/or provided in a yield of at least about 60%, 65%, 70%, 75%, 80%, 90%, 95%, or more.

A method of the present disclosure may provide ribitol (e.g., isolated ribitol) having a purity of at least about 70%, 75%, 80%, 85%, 90%, 95%, or about 100%. For example, in some embodiments, ribitol is obtained and/or provided having a purity of at least about 70%, 75%, 80%, 85%, 90%, 95%, 96%, 97%, 98%, 99%, 99.5%, 99.8%, 99.9%, or about 100%. In some embodiments, ribitol is obtained having a purity of at least 90%.

The present subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

The term "substantially pure ribitol" refers to the total absence, or near total absence, of impurities, such as related-substance impurities. For example, when a ribitol composition is said to be substantially pure, there are either non detectable impurities, or if a single impurity is detected, it is present in an amount no greater than 0.1% by weight, or if multiple impurities are detected, they are present in aggregate in an amount no greater than 0.3% by weight.

In some embodiments, the ribitol composition does not contain any impurity at a concentration of greater than about 0.01%, 0.05%, 0.1%, 0.2%, 0.3%, 0.4%, 0.5%, 1%, 2%, 5%, 7%, 10%, 15%, 20%, 25%, or 30% by weight.

In some embodiments, the ribitol composition does not contain multiple impurities at a concentration of greater than about 0.1%, 0.2%, 0.3%, 0.4%, 0.5%, 1%, 2%, 5%, 7%, 10%, 15%, 20%, 25%, or 30% by weight.

The term "substantially free of" may mean that the ribitol composition is at least about 99% free of nickel, platinum, palladium, ruthenium, sodium, boric acid, trifluoroacetic acid, D-Arabitol and/or any combination thereof. In some embodiments, the analytical purity of ribitol is at least 99.7%. In further embodiments, the ribitol composition is completely free of nickel, platinum, palladium, ruthenium, sodium, boric acid, trifluoroacetic acid, and D-Arabitol.

In some embodiments, the ribitol composition is substantially free of nickel, platinum, palladium, ruthenium, sodium, boric acid, trifluoroacetic acid, D-Arabitol and/or any combination thereof.

In some embodiments, the ribitol composition is substantially free of sodium salts. In some embodiments, the ribitol composition is substantially free of boric acid. In some embodiments, the ribitol composition is substantially free of trifluoroacetic acid. In some embodiments, the ribitol composition is substantially free of D-Arabitol.

In some embodiments, the disclosure provides a pharmaceutical composition for use as a therapeutic comprising substantially pure ribitol. In some embodiments, the ribitol composition is substantially free of nickel, platinum, palladium, ruthenium, sodium, boric acid, trifluoroacetic acid, D-Arabitol and/or any combination thereof.

In some embodiments, the disclosure provides a pharmaceutical composition for use as a therapeutic comprising substantially pure ribitol wherein the composition does not contain any impurity at a concentration of greater than about 0.1% by weight. The disclosure further provides aa pharmaceutical composition for use as a therapeutic comprising substantially pure ribitol wherein the composition does not contain any impurity at a concentration of greater than 0.01% by weight.

In some embodiments, the disclosure provides a pharmaceutical composition for use as a therapeutic comprising substantially pure ribitol wherein the total amount of impurities present in the composition is less than about 0.3% by weight. The disclosure further provides a pharmaceutical composition for use as a therapeutic comprising substantially pure ribitol wherein the total amount of impurities present in the composition is less than about 0.03% by weight.

In some embodiments, the disclosure provides a pharmaceutical composition of ribitol for use as a therapeutic wherein the composition has a residual lithium amount of less than about 550 ppm. In some embodiments, a pharmaceutical composition of ribitol for use as a therapeutic has a residual lithium amount of less than about 100 ppm.

In some embodiments, the disclosure provides a pharmaceutical composition of ribitol for use as a therapeutic wherein the composition has a residual citric acid amount of less than about 20,000 ppm. In some embodiments, a pharmaceutical composition of ribitol for use as a therapeutic has a residual citric acid amount of less than about 3400 ppm.

In some embodiments, the disclosure provides a pharmaceutical composition of ribitol for use as a therapeutic wherein the composition has a residual methanol amount of less than about 5,000 ppm. In some embodiments, a pharmaceutical composition of ribitol for use as a therapeutic has a residual methanol amount of less than about 1850 ppm.

In some embodiments, the disclosure provides a pharmaceutical composition of ribitol for use as a therapeutic wherein the composition has a residual 1-propanol amount of less than about 5,000 ppm. In some embodiments, a pharmaceutical composition of ribitol for use as a therapeutic has a residual 1-propanol amount of less than about 500 ppm.

In some embodiments, the disclosure provides a pharmaceutical composition of ribitol for use as a therapeutic wherein the composition has a residual boron amount of less than about 3,000 ppm. In some embodiments, a pharmaceutical composition of ribitol for use as a therapeutic has a residual boron amount of less than about 300 ppm.

In some embodiments, the disclosure provides a pharmaceutical composition comprising excipients and carriers described herein in further detail. In some embodiments, the excipients are pharmaceutically acceptable.

The excipients are chosen such that they are compatible with ribitol, i.e. such that there is no or only marginal degradation of ribitol in the pharmaceutical composition. The degradation can be tested in standard tests, for example after a 6 months storage at 40° C. and 75% relative humidity. In this context, the term "marginal degradation" shall mean a chemical degradation of ribitol of less than 5%, less than 3%, or less than 2% by weight of ribitol. The content and thus the degradation can be determined by well-known analytical methods, for example using HPLC or UV methods.

In the pharmaceutical composition according to the disclosure, the excipients may comprise one or more diluents, binders, disintegrants, lubricants and/or any combination thereof. Excipients may have two or more functions at the same time, for example may act as a diluent and as a binder or as a binder and as disintegrant or as a diluent, as a binder and as disintegrant.

Common excipients include but are not limited to mannitol, pregelatinized starch, copovidone, cornstarch, Maize starch, crospovidone, magnesium stearate, and talc.

The one or more diluents, another term is filler, are added as the quantity of the active pharmaceutical ingredient(s) is small and thus to achieve a minimal tablet weight (for example 100 mg or more) and a satisfying content uniformity (for example <3% standard deviation) according to the pharmacopeias. Common diluents include but are not limited to lactose, sucrose, and microcrystalline cellulose. The one or more diluents suitable for a pharmaceutical composition according to the disclosure are selected from the group consisting of cellulose, in particular cellulose powder, dibasic calciumphosphate, in particular anhydrous or dibasic calciumphosphate dihydrate, erythritol, mannitol, starch, pregelatinized starch, glycerin, and xylitol, including derivatives and hydrates of the beforementioned substances. The diluents pre-gelatinized starch shows additional binder properties.

The pharmaceutical composition also includes other pharmaceutically acceptable carriers and/or excipients such as binders, lubricants, diluents, coatings, disintegrants, barrier layer components, glidants, coloring agents, solubility enhancers, gelling agents, fillers, proteins, co-factors, emulsifiers, solubilizing agents, suspending agents and mixtures thereof.

A person skilled in the art would know what other pharmaceutically acceptable carriers and/or excipients could be included in the formulations according to the invention. Appropriate excipients are known to those skilled in the art (see Handbook Of Pharmaceutical Excipients, fifth edition, 2005 edited by Rowe et al., McGraw Hill).

In some embodiments, appropriate excipients include but are not limited to: lubricants such as magnesium stearate, stearic acid, sodium stearyl fumarate and mixtures thereof; microcrystalline cellulose, cross-linked sodium carboxymethylcellulose, corn starch, and mixtures thereof coating, binding and gelling agents such as hydroxypropyl methocellulose (HPMC);

PEG-fatty acid esters include those with a molecular weight up to 8000 and the fatty acid component can be selected from any suitable fatty acid such as laurate, dilaurate, oleate, stearate, glycerol trioleate, dioleate, glyceryl laurate, glyceryl oleate, palm kernel oil, hydrogenated castor oil, caster oil, corn oil, caprate/caprylate glycerides, polyglyceryl-10 laurate, phytosterols, cholesterol, soya sterol, sorbitan oleate, sorbitan laurate and mixtures thereof.

In some embodiments, the pharmaceutical composition is a unit dose form comprising one or more of a plurality of granules, pellets, particles or mini-tablets.

In some embodiments, the pharmaceutical composition is a unit dose form comprising about 1 mg to about 12 g of substantially amorphous or amorphous ribitol.

In some embodiments, the pharmaceutical composition of substantially pure ribitol is administered a patient in need thereof.

Administration of the pharmaceutical composition may be oral, buccal, sublingual, topical, parenteral, or enteral. The compositions of the disclosure are suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal, intravenous, intraarterial, intrathecal, intraventricular, intraurethral, intracranial, intratumoral, intrasynovial injection or infusions; and kidney dialytic infusion techniques. In some embodiments, parenteral administration of the compositions of the present disclosure comprises intravenous administration.

Formulations of a pharmaceutical composition suitable for parenteral administration may comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the components of the formulation.

In some embodiments, the pharmaceutical composition is a unit dose form comprising about 1 mg, about 5 mg, about 10 mg, about 50 mg, about 100 mg, about 200 mg, about 300 mg, about 400 mg, about 500 mg, about 600 mg, about 700 mg, about 800 mg, about 900 mg, about 1 g, about 1.5 g, about 2 g, about 3 g, about 4 g, about 5 g, about 6 g, about 7 g, about 8 g, about 9 g, about 10 g, about 11 g, or about 12 g of substantially amorphous or amorphous ribitol.

EXAMPLES

The following EXAMPLES provide illustrative embodiments. Certain aspects of the following EXAMPLES are disclosed in terms of techniques and procedures found or contemplated by the present inventors to work well in the practice of the embodiments. In light of the present disclosure and the general level of skill in the art, those of skill will appreciate that the following EXAMPLES are intended to be exemplary only and that numerous changes, modifications, and alterations can be employed without departing from the scope of the present disclosure.

Example 1

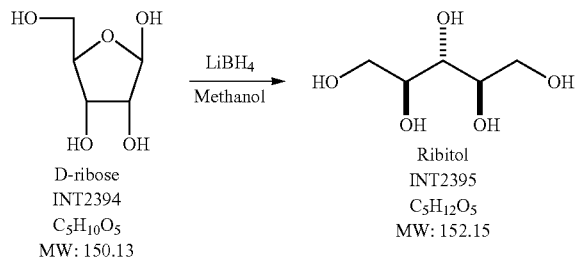

Scheme 1: Synthesis scheme of reduction of D-ribose to Ribitol

D-ribose
INT2394
$C_5H_{10}O_5$
MW: 150.13

Ribitol
INT2395
$C_5H_{12}O_5$
MW: 152.15

General Procedure:

1. Inert the reactor and charge with INT2394 (1.00 eq) and methanol (2.5 vol).
2. Start stirring the reactor contents at appropriate speed.
3. Cool the reactor contents to 10±5° C.
4. Charge lithium borohydride (0.038 eq) and keep the temperature between 20±10° C.
5. Stir the reactor contents until the gas evolution stops and the internal temperature is 10±5° C.
6. Charge another 9 portions of lithium borohydride as described in steps 4 and 5.
7. Perform a line rinse with methanol (0.5 vol).
8. Stir the mixture for at least 3 hours at 20±5° C.
9. Sample the reaction mixture in order to check the conversion by HPLC (specification:
   HPLC conversion: ≥97 area-% INT2395; IPC-1A).
10. Charge citric acid (0.48 eq) and inert the reactor.
11. Stir the mixture for 45±15 minutes at 20±5° C.
12. Heat the reactor contents to 55±5° C.
13. Stir the mixture for 15±10 minutes at 5±5° C.
14. Check if a solution is obtained.
15. Install a suitable filter cartridge with mesh 0.2 μm in CUNO filter F1.
16. Rinse the second reactor and the filter with a suitable amount of methanol.
17. Disassemble and clean the bottom valve of the second reactor manually.
18. Release the contents of the first reactor to the second reactor via F1 and filter the solution (rinse).
19. Adjust the temperature in the second reactor to 55±5° C.
20. Rinse the first reactor, inline filter and the lines with methanol (0.5 vol) and transfer this to the second reactor.
21. Cool the reactor contents to 25±5° C. in 75±15 minutes.
22. Stir the mixture for at least 90 minutes at 25±5° C.
23. Check if crystallization has occurred.
24. Cool the reactor contents to 0±5° C. in 45±15 minutes.
25. Stir the mixture for at least 60 minutes at 0±5° C.
26. Release the contents of the reactor to the filter and filter the suspension. Transfer the mother liquor to a new drum.
27. Charge the reactor with 1-propanol (2.0 vol).
28. Release the reactor contents to the filter (wash 1) and transfer the mother liquor to a new drum.
29. Charge the reactor with 1-propanol (2.0 vol).
30. Release the reactor contents to the filter (wash 2) and transfer the mother liquor to a new drum.
31. Charge the reactor with 1-propanol (2.0 vol).
32. Release the reactor contents to the filter (wash 3) and transfer the mother liquor to a new drum.
33. Charge the reactor with 1-propanol (2.0 vol).
34. Release the reactor contents to the filter (wash 4) and transfer the mother liquor to a new drum.
35. Dry the contents on the filter by vacuum and/or nitrogen flow for at least 8 hours at 40±5° C.
36. Sample the filter cake in order to determine the solvents by HSGC (specification: solvents (HSGC): 1-propanol≤5000 ppm and methanol≤3000 ppm; IPC-2A).
37. Sample the filter cake for release testing of INT2395 (IPC-3) and transfer the product in one or more HDPE drums lined with double PE bags. Release the material when it complies with the following specifications: Appearance: Report result; HPLC purity: >97.0 area-%; $^1$H-NMR identity: conform structure, $^1$H-NMR-assay: report result, Residual solvents: report result; Residual citric acid: ≤20000 ppm; Residual elements: B≤1000 ppm, Li≤500 ppm.

A 1.18 kg (78%) of batch of ribitol was harvested. The appearance was white powder, no visible impurities. The HPLC purity was 99.9 area-%; the $^1$H-NMR was conform structure, the $^1$H-NMR assay was 100.7 wt-%; arabitiol was not detected; ribose was not detected; the residual solvents were 1820 ppm for methanol and <500 ppm for 1-propanol; the residual citric acid was 3320 ppm; the residual elements were 268 ppm for B and 100 ppm for Li.

This method gave full conversion with the added advantages of using concentrated conditions in a solvent that would facilitate both screening and crystallization and which could be easily removed. The challenge for this method was in removing residual salts originating from the use of the borohydride reagent. The method developed is a scalable process that was successful in affording the desired product in high yield and in purging all residual impurities to well within acceptable levels. The process is extremely efficient and able to successfully synthesize a 1 kg demonstration batch in good yield (78%) and excellent purity (99.9 area-%).

The foregoing is illustrative of the present disclosure and is not to be construed as limiting thereof. Although a few exemplary embodiments of this disclosure have been described, those skilled in the art will readily appreciate that many modifications are possible in the exemplary embodiments without materially departing from the novel teachings and advantages of this disclosure. Accordingly, all such modifications are intended to be included within the scope of this disclosure as defined in the claims. The disclosure is defined by the following claims, with equivalents of the claims to be included therein.

That which is claimed is:

1. A method of making ribitol comprising:
   combining a reductive borohydride and D-ribose, optionally with stirring, to form a first reaction mixture; and
   contacting the first reaction mixture with an acidic quenching agent, optionally with stirring, to form a second reaction mixture, thereby forming ribitol.

2. The method of claim 1, wherein the reductive borohydride is selected from the group consisting of lithium borohydride ($LiBH_4$), sodium borohydride ($NaBH_4$), zinc borohydride ($Zn(BH_4)_2$), calcium borohydride ($Ca(BH_4)_2$), sodium triacetoxyborohydride ($NaBH(OAc)_3$), sodium cyanoborohydride ($NaBH_3CN$), lithium aluminum hydride, potassium borohydride ($KBH_4$), and any combination thereof.

3. The method of claim 1, wherein contacting the first reaction mixture and the acidic quenching agent comprises adding the acidic quenching agent in an amount of about 0.3-0.6 molar equivalents relative to D-ribose.

4. The method of claim 1, wherein the first reaction mixture and/or the second reaction mixture are non-aqueous and/or wherein the method of making ribitol is carried out with non-aqueous compositions.

5. The method of claim 1, wherein the acidic quenching agent is selected from the group consisting of citric acid, formic acid, acetic acid, trifluoroacetic acid, hydrochloric acid, oxalic acid, propionic acid, pyruvic acid, methanesulfonic acid, trifluoromethanesulfonic acid, a C1-5 carboxylic or dicarboxylic acid, and any combination thereof.

6. The method of claim 1, wherein the reductive borohydride comprises lithium borohydride and wherein the acidic quenching agent comprises citric acid.

7. The method of claim 1, wherein the first reaction mixture and/or the second reaction mixture further comprise an organic solvent.

8. The method of claim 7, wherein the organic solvent is selected from the group consisting of ethanol, methanol, propanol, and any combination thereof.

9. The method of claim 1, wherein:
   (i) combining the reductive borohydride and D-ribose is carried out at a temperature of about 5° C.-35° C., optionally under cooling conditions; and/or
   (ii) the method further comprises heating the second reaction mixture, optionally with stirring, to a temperature of about 40° C.-65° C.

10. The method of claim 1, wherein the second reaction mixture comprises about 1-5 relative volumes of an organic solvent and/or an acid quench is carried out in about 1-5 relative volumes of an organic solvent.

11. The method of claim 1, furthering comprising isolating ribitol from the second reaction mixture to obtain an isolated ribitol.

* * * * *